United States Patent
Morgan et al.

(10) Patent No.: US 7,573,974 B2
(45) Date of Patent: Aug. 11, 2009

(54) DEVICE AND METHOD FOR NON-CONTACT SCANNING OF CONTACT LENS AND CONTACT LENS MOLD GEOMETRY

(75) Inventors: Courtney Flem Morgan, Alpharetta, GA (US); William Jordan Hall, Atlanta, GA (US)

(73) Assignee: Novartis AG, Basel (CH)

( * ) Notice: Subject to any disclaimer, the term of this patent is extended or adjusted under 35 U.S.C. 154(b) by 254 days.

(21) Appl. No.: 11/359,256

(22) Filed: Feb. 22, 2006

(65) Prior Publication Data

US 2007/0195311 A1    Aug. 23, 2007

(51) Int. Cl.
*G01N 23/00* (2006.01)

(52) U.S. Cl. .......................................... 378/4

(58) Field of Classification Search ................. 356/124, 356/600, 432, 239.2; 378/4, 19, 51, 58, 62
See application file for complete search history.

(56) References Cited

U.S. PATENT DOCUMENTS

| | | | |
|---|---|---|---|
| 5,559,848 A * | 9/1996 | Collins ..................... 378/58 |
| 6,072,570 A * | 6/2000 | Chipman et al. ............ 356/124 |
| 6,113,817 A | 9/2000 | Herbrechtsmeier et al. |
| 6,765,661 B2 * | 7/2004 | Biel et al. .................... 356/124 |
| 6,917,665 B2 | 7/2005 | Nakanishi et al. |
| 6,944,261 B2 | 9/2005 | Adachi et al. |
| 6,957,095 B2 | 10/2005 | Matsui |
| 6,987,827 B2 | 1/2006 | Tsukagoshi |
| 6,990,168 B2 | 1/2006 | Tsukagoshi et al. |
| 6,990,170 B2 | 1/2006 | Sugihara et al. |
| 6,990,175 B2 | 1/2006 | Nakashima et al. |
| 7,215,736 B1 * | 5/2007 | Wang et al. ................... 378/25 |
| 2004/0189981 A1* | 9/2004 | Ross et al. .................. 356/124 |
| 2006/0132761 A1* | 6/2006 | Hall ........................... 356/124 |
| 2006/0146316 A1* | 7/2006 | Hong ......................... 356/124 |
| 2006/0176491 A1* | 8/2006 | Hall ........................... 356/601 |

OTHER PUBLICATIONS www.skyscan.be; SkyScan1172 high-resolution micro-CT; (date unknown); 3 pgs.
www.skyscan.be; SkyScan1173 high energy micro-CT; (date unknown); 3 pgs.
www.skyscan.be; SkyScan1174 compact micro-CT; (date unknown); 3 pgs.
www.skyscan.be; SkyScan 1076 in-vivo micro-CT; (date unknown); 2 pgs.
www.skyscan.be; SkyScan1178 high-throughput micro-CT; (date unknown); 2 pgs.

* cited by examiner

*Primary Examiner*—Kara E Geisel
(74) *Attorney, Agent, or Firm*—Robert Ambrose

(57) ABSTRACT

The invention relates to an apparatus and method for non-contact/non-destructive measurement of the geometry of molded ophthalmic lenses and the precision molds and tooling used in the manufacture of the ophthalmic lenses. In particular the present system uses micro computed tomography to measure the geometries.

9 Claims, 4 Drawing Sheets

DEVICE AND METHOD FOR NON-CONTACT SCANNING OF CONTACT LENS AND CONTACT LENS MOLD GEOMETRY

FIELD OF THE INVENTION

This invention relates to an apparatus and method for non-contact/non-destructive measurement of the geometry of molded ophthalmic lenses and the precision molds and tooling used in the manufacture of the ophthalmic lenses. In particular the present system uses micro computed tomography to measure the geometries.

BACKGROUND OF THE INVENTION

Ophthalmic lenses may be created using a variety of methods, one of which includes molding. In a double sided molding process, the lenses are manufactured between two molds without subsequent machining of the surfaces or edges. Such mold processes are described, for example in U.S. Pat. No. 6,113,817, which is expressly incorporated by reference as if fully set forth herein. As such, the geometry of the lens is determined by the geometry of the mold. Typical molding systems include cast molding, which involves using two mold halves, and spin-casting. These methods may also be combined with other machining techniques to create specific lens designs. Another process involves cycling lenses through a series of stations on a semi-continuous basis. The cyclic portion of lens production generally involves dispensing a liquid crosslinkable and/or polymerizable material into a female mold half, mating a male mold half to the female mold half, irradiating to crosslink and/or polymerize, separating the mold halves and removing the lens, packaging the lens, cleaning the mold halves and returning the mold halves to the dispensing position.

Once a mold is designed and fabricated it must be measured to ensure that it meets the proper specifications. Additionally, the mold material affects the end product, as the mold material may undergo non-uniform shrinkage as the mold is cured. Defects such cylinder and differential shrinkage are difficult to measure and characterize currently. The molded lenses must also be measured to ensure they are formed in the desired shape. The desired lens geometry may be spherical or non-spherical. The cured lens will not reflect the precise geometry of the mold due to volumetric shrinkage of the lens material. As the lens material cures, the arcuate surfaces of the lens result in a complex 3-dimensional change in the lens geometry from that of the mold.

The determination of the mold and lens geometries presents many challenges. A molded contact lens will distort under its own weight. The lens must then be supported by an optical tool to measure the lens geometry. The optical tool can distort the lens and result in an inaccurate measurement of the true lens geometry. Of particular difficulty is the measurement of the base curve of the lens. The base curve is the inner curved surface which contacts the eye. To compound the problems, the lens must also be kept hydrated during the measurement process to avoid shrinkage and distortion associated with the liquid content of the lens. Osmolarity, pH and temperature effects should also be considered or controlled when assessing the lens geometry.

Current techniques used to measure the lens and mold geometry include scanners such as vision, laser scan, interferometer, or touch probe. These techniques are difficult, slow, often inaccurate, and lack desired functionality. The lens or mold sample must be precisely positioned within the scanner or the accuracy of the measured geometry will be adversely affected. Most commercially available scanner technologies cannot capture a large area, such as the entire 14 mm diameter of a lens, and are only able to inspect a portion of the sample geometry at a time. The vision systems and lasers must have a direct line of sight with the surface being measured, which is not always possible on the arcuate surfaces of the contacts lenses, lens molds, and optical tooling. One example where direct line of sight is not possible is the base curve surface of a contact lens. The base curve surface is obscured from direct line of sight measurement by other portions of the surface. The touch probe scanning technique is a contact technique and involves correcting for induced changes in geometry as the compliant lens is deformed by the probe. Because of the direct line of sight or access requirement, the current techniques cannot inspect an object within an object, such as a lens clamped within a mold assembly.

Computed Tomography (CT) scanning is a well accepted method of medical imaging. The method uses a source of electromagnetic radiation, typically X rays, and a detector. An object to be scanned is positioned between the radiation source and the detector such that a portion of the electromagnetic radiation passes through the object before being received by the detector. The intensity of scattered and transmitted electromagnetic radiation is then measured at each pixel of the detector. The radiation intensity values at each pixel are then processed to form an image of the object being scanned. The source and detector are rotated through a specific path around the object being scanned and a number of X-ray images are collected. The intensity values for each image are then processed on a computer and utilizing the geometrical relationship between the source and detector, object surfaces are reconstructed to create a three dimensional geometric model of the scanned object. In an alternative approach, the sample is rotated relative to the source and detector while the X-ray images are taken. This approach is generally referred to as micro-Computed Tomography or microCT. In recent years, the resolutions of the resulting scans has increased to anywhere from 15 microns to 150 nanometers using high resolution, low cost imaging chips and the speed of the reconstruction of the data has greatly increased with faster computers.

SUMMARY OF THE INVENTION

The present invention seeks to provide a non-contact, non-destructive method and apparatus for determining the geometry of molded ophthalmic lenses and the precision molds and tooling used in the manufacture of the ophthalmic lenses. In particular the present system uses micro computed tomography to measure the geometries. In one embodiment of the present invention, an ophthalmic sample may include a contact lens, a contact lens mold, or an optical tool. The method for measuring the precise geometry of the ophthalmic sample may include providing a source of electromagnetic radiation at an intensity, providing a detector to detect the electromagnetic radiation intensity, positioning the sample such that the electromagnetic radiation generated by the source passes through the sample and to the detector, detecting the electromagnetic radiation intensity after passing through the sample, and processing the electromagnetic radiation intensity detected to obtain a 2-dimensional image of the sample.

In a further embodiment, the positioning step includes placing the sample on a rotatable platform, the sample then being rotated to a plurality of orientations by the rotating platform. The detecting step further includes detecting the electromagnetic radiation intensity for each orientation of the sample, and the processing step further includes processing the electromagnetic radiation intensity detected for each orientation of the sample to obtain a 3-dimensional model of the sample surfaces, with the model representing the precise 3-dimensional geometry of the sample surfaces.

In a further embodiment, the processing step further includes applying a sub-pixel edge detection algorithm to the measured electromagnetic radiation intensity. In another embodiment, the positioning step occurs on a manufacturing line. In another embodiment, the positioning step includes positioning a contact lens on a human eye. In another embodiment, the electromagnetic radiation is in the range of 1 micrometer to 0.1 nanometer.

The method of the present invention may also include the step of archiving the precise geometry of the sample surfaces in a database application. Additionally, the method may include the step of using the processed sample surface geometry in a feedback process to iteratively modify the geometry of a lens mold, or an optical tool. Additionally, the method may include the step of using the processed sample surface geometry to iteratively modify a non-geometric parameter of the manufacturing process. The method may also include the step of applying a contrast agent to the sample prior to exposure to the electromagnetic radiation.

In the method of the present invention, the sample may include a contact lens in a retail package. In another embodiment of the method, the sample may be partially surrounded by a saline solution. In yet another embodiment of the method, the sample includes at least two of the group comprising a contact lens, a contact lens mold, or an optical tool.

The present invention also includes an apparatus for measuring the precise geometry of an ophthalmic sample. The ophthalmic sample may be a contact lens, a contact lens mold, an intraocular lens or an optical tool. The apparatus may include a source of electromagnetic radiation at an intensity, a detector to detect the electromagnetic radiation intensity, a fixture for positioning the sample such that the electromagnetic radiation generated by the source passes through the sample and to the detector, a detecting means for detecting the electromagnetic radiation intensity after passing through the sample, and a processing means for processing the electromagnetic radiation intensity detected to obtain a 2-dimensional image of the sample.

In a further embodiment, the fixture for positioning the sample includes a rotatable platform capable of rotating the sample to a plurality of orientations. The detecting means being capable of detecting the electromagnetic radiation intensity for each orientation of the sample, and the processing means processing the electromagnetic radiation intensity detected for each orientation to obtain a 3-dimensional model of the sample surfaces. The model then representing the precise 3-dimensional geometry of the sample surfaces.

In a further embodiment, the processing means includes a means for applying a sub-pixel edge detection algorithm to the electromagnetic radiation intensity. In another embodiment, the rotatable platform includes more than one rotational stage. In another related embodiment, the rotatable platform includes a first rotational stage axis and an orthogonal second rotational stage axis. In another related embodiment, the rotatable platform may be a Stewart platform, or a parallel kinematics motion stage.

In further embodiments, the electromagnetic radiation source is capable of producing electromagnetic radiation in the range of 1 micrometer to 0.1 nanometer. The apparatus processing means may include a personal computer. In a related embodiment, the processing means may include a database for archiving the precise geometry of the sample surfaces.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

Reference now will be made in detail to the embodiments of the invention. It will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

The present invention comprises an apparatus and method to more accurately measure the precise geometry of ophthalmic lenses, lens molds or optical tools used in the lens manufacture. In a preferred embodiment, the present invention is able to accurately scan and reconstruct the surface geometry of the entire ophthalmic lens including the base curve optical surface. The invention can also accurately scan and reconstruct the optical surfaces of the molds used in forming the lens and the surfaces of optical tools used in the manufacturing process. The invention comprises a microCT scanner used to conduct a high resolution scan of a sample ophthalmic lens, lens mold or optical tool at a given orientation. The present invention also includes a rotatable platform to rotate the sample to multiple orientations relative to the scanner for additional scans, and a processing means to compute a precise three dimensional representation of the object.

Figure 1:
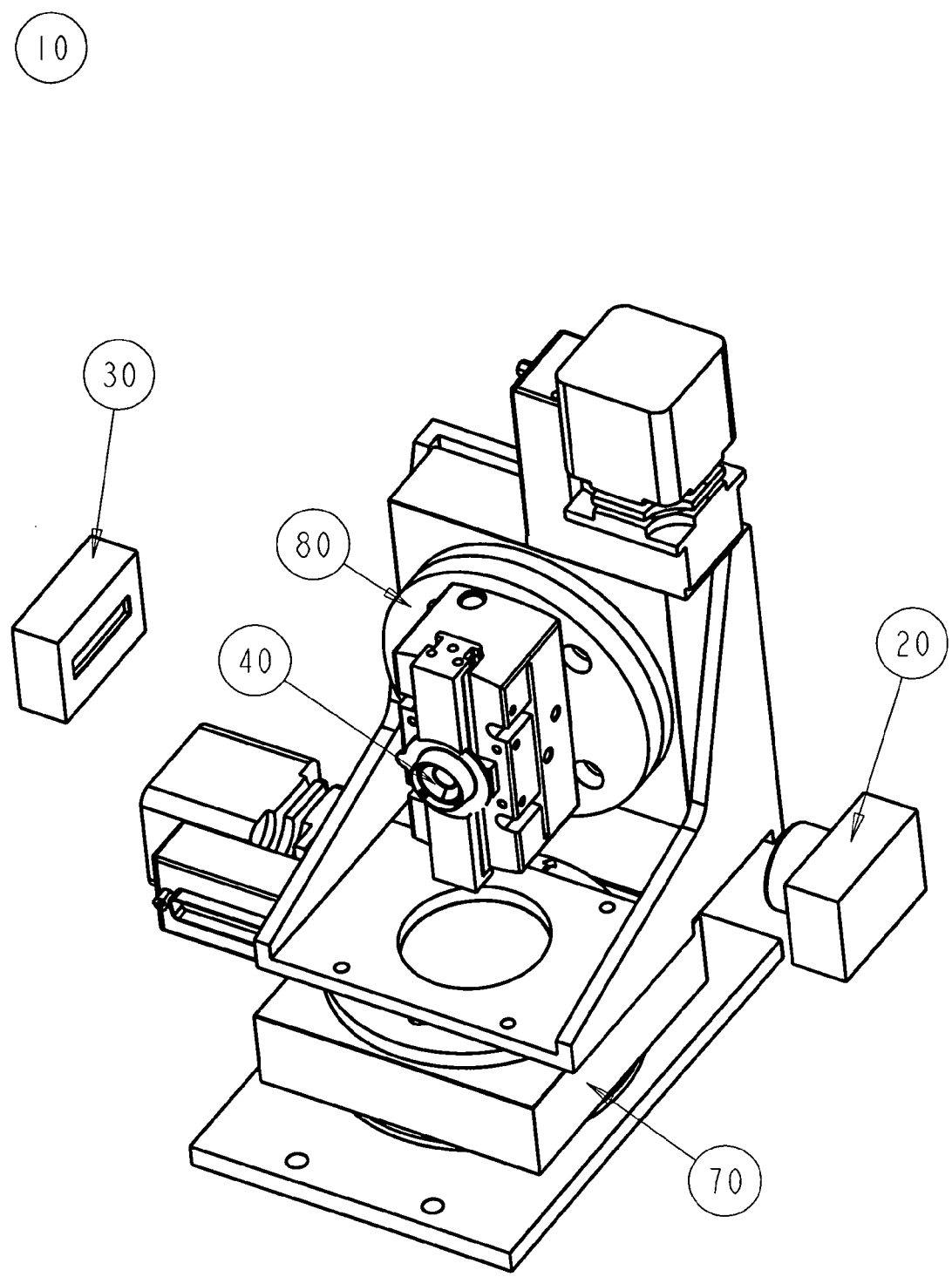
FIG. 1 is a perspective illustration of one embodiment of the present invention.

FIG. 1 depicts a general configuration of the apparatus of the present invention. A micro-computed tomography scanner 10 comprises an x-ray source 20, an x-ray detector 30, an object chamber 40 placed between the x-ray source 20 and the detector 30, and a computer that controls the x-ray radiation and detector data collection. A sample is placed within the object chamber 40 for scanning. In this embodiment a first rotary stage 70 is used within the object chamber 40 to rotate the sample to multiple orientations for data collection. A second rotary stage 80 is preferably used with the axis of rotation orthogonal to the first rotary stage 70. The first and second rotary stages 70, 80 may then be used to position the sample in any desired orientation relative to the source and detector for data collection.

In one embodiment, a commercially available micro Computed Tomography system may be used to scan the ophthalmic sample. Examples of such scanners include, for example, the SkyScan as manufactured by SkyScan (Aartselaar, Belgium http://www.skyscan.be) or the Konoscope as manufactured by ARACOR (Hawthorne, Calif. http://www.aracor.com)

In a more preferred embodiment, a system similar to the SkyScan-1072 may be used. A preferred resolution may average approximately 8 microns. Resolutions in the range of about 15 microns to about 150 nanometers are readily available with high resolution commercial systems. The optical surfaces of interest for the ophthalmic lenses and molds average about 14 millimeters in diameter and approximately about 9 millimeters in height. The SkyScan unit uses a cone-beam X-ray source, wherein the beam expands as it moves from the source to the detector. The accuracy of the system is dependent on the size of the object being scanned and the distance of the object from the source. In scanning objects of size of ophthalmic lenses and molds, the SkyScan-1072 may yield a pixel size of approximately 8 microns, and a dimensional accuracy of approximately 8 microns.

In one embodiment of the invention, the effective resolution and dimensional accuracy of each image scan can be increased using mathematical methods commonly known in the art as sub-pixel edge detection techniques. Edge detection refers to the process of identifying and locating discontinuities in an image. The boundaries of objects are indicated by abrupt changes in pixel intensity. There are many different types of edge detection operators known in the art. In one method, an edge is detected by a change in the intensity profile of the pixels above or below a given percentage threshold of the average pixel intensity in the region of interest. The intensity profile may change over several pixels and the actual location of the edge is a matter of interpretation. The edge may be defined at the beginning, the end, or the midpoint of the contact gradient where the intensity profile change exceeds the threshold value. Mathematical methods may be applied to the intensity profile to determine the edge location to a finer resolution than supplied by the pixel widths in the scan. The computed edge location may fall between individual pixels and is therefore referred to as sub-pixel edge detection. The SkyScan-1072 may yield a dimensional accuracy in the range of 2.0 to 0.5 microns when sub-pixel edge detection methods are employed in scanning the samples of interest in the invention.

As further shown in FIG. 1, in one embodiment, a sample may be placed on a rotational is platform of some type within the object chamber. The rotational platform is adapted to hold the sample securely while providing rotational movement. In a specific embodiment, the invention may have two rotational stages (a first rotational stage 70 and a second rotational stage 80) mounted at approximately 90 degrees relative to each other to provide rotational movement. In this embodiment a bracket is preferably mounted to the movement platform of first stage 70 to allow the entire bracket to rotate. The second stage 80 is preferably mounted to bracket 120. Ophthalmic sample 40 is preferably mounted on the platform of second stage 80. By rotating both stages, the sample may be pivoted to a plurality of orientations for scanning. In this arrangement, the first stage 70 preferably provides the tilt and the second stage 80 preferably moves the ophthalmic sample through different meridians or semi-meridians. In a preferred setup of this embodiment, a Stewart platform or a parallel kinetics motion stage may be used.

Figure 2:
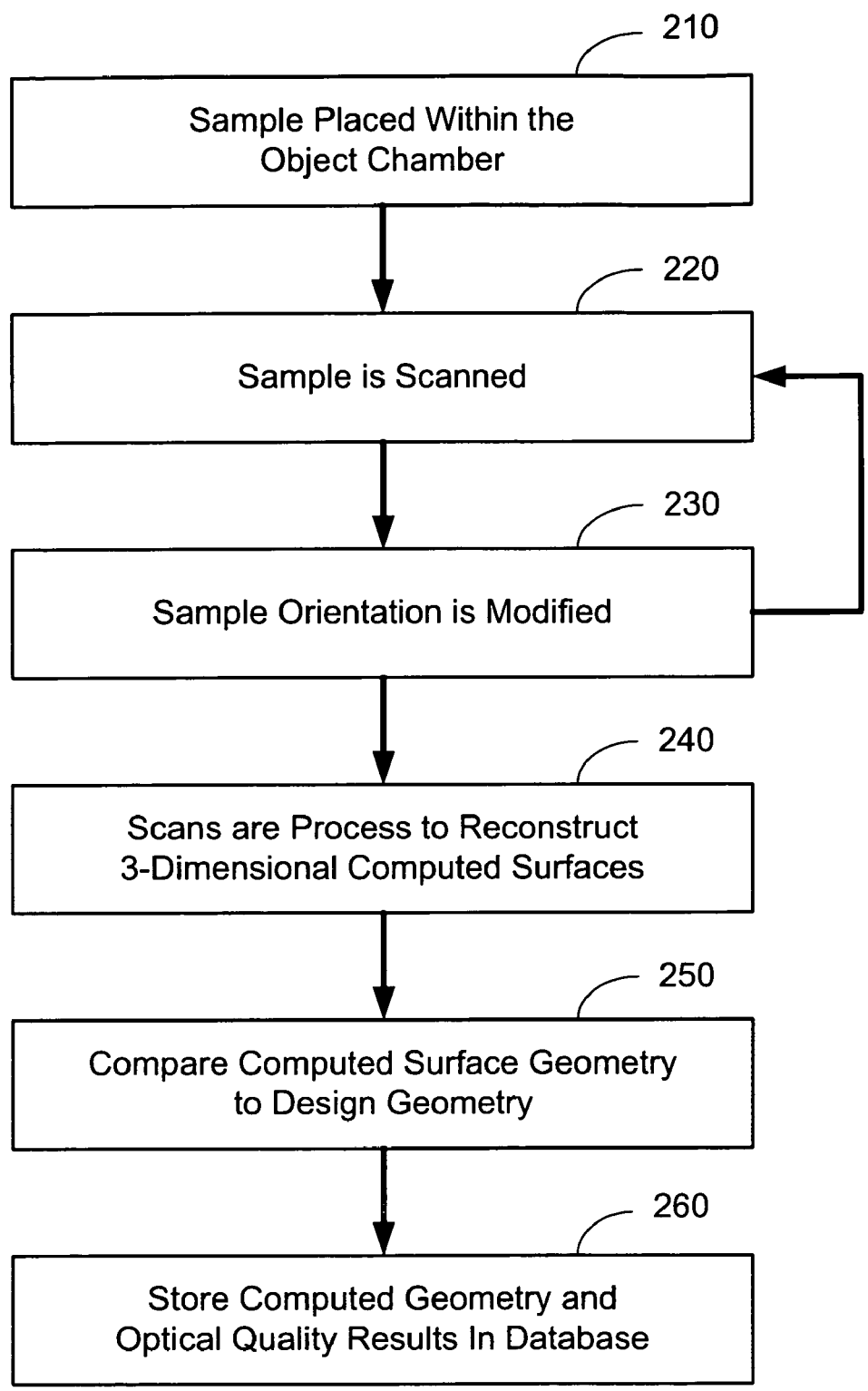
FIG. 2 is a flowchart of exemplary steps used in the methods of the present invention.

The method of the present invention is depicted in FIG. 2. Referring to FIG. 2, in one embodiment of the method of the present invention, the geometry of a front curve mold sample is measured. The sample is first placed within the object chamber upon the rotatable platform 210. The alignment of the sample upon the platform will not adversely affect the accuracy of the resulting scans and is therefore not critical.

The sample is then scanned in step 220. Next, in step 230, the sample may be tilted or rotated while additional scans 220 are captured at desired angular orientations. Steps 220 and 230 may be performed in one or more loops to produce sufficient data to fully characterize the sample.

In step 240, all of the scans may be analyzed, processed, and reconstructed as 3-dimensional computed surfaces of the sample scanned in steps 220. The computed surfaces created may be limited to the optical surfaces of interest in the sample, in this example the front curve inner surface, or may be a representation of all surfaces in the sample. After the 3-dimensional representation is created, an optical quality comparison may be generated in step 250 by comparing the computed geometry of the representation of the sample to an idealized geometry. A full 3-dimensional representation of the sample surfaces may not be required to be calculated. Instead a 2-dimensional slice through the sample may provide the required optical surface dimensional measurements. The calculation of the geometry of only a slice of the object will increase the computational efficiency of the process. In step 260, the computed geometry and/or the optical quality evaluation may be sent to a database application.

These steps may not need to be performed in the exact order described above, but rather, may be performed in any logical progression.

In an alternative embodiment of the present invention each scan of the sample may not be processed to reconstruct a 3-dimensional representation of the object. The radiation intensity data gathered for a particular scan, or group of scans, may be processed to form images of the sample. The resulting images may be visually inspected by an operator. The radiation intensity data may also be processed by mathematical algorithms to inspect the sample, and identify possible defects within the sample. Such defects may include, but are not limited too; entrained gas bubbles, inclusions, or contaminants within the molded lens or the lens molds, polymer remaining on a lens mold after the molded lens is removed, and contaminants present on an optical tool.

The measurement system is preferably controlled through a PC. The computer software reconstructs or computes the 3-dimensional surfaces of the sample by using the series of projection images collected from different sample orientations. The data output generated by the present invention is very flexible. The system may return the exact shape of the entire sample. Parameters such as curvature of an optical surface may be calculated. Calculations of the complex 3-dimensional shrinkage occurring in the sample can be generated. Individual data slices may also be potted from the data. Because the computed surface can be interpolated, the user can select a particular slice of the surface. Also, simplified measurements such as radius over a specific diameter or polynomial fits can be applied to the data. The computed 3-dimensional surface data may be compared to an idealized mathematical representation of the surface, and the deviation of the actual surface from the design surface can be quantified and plotted.

In addition to graphics, underlying statistics and data can be output to a document or spreadsheet. The data can also be archived for future use.

Figure 3:
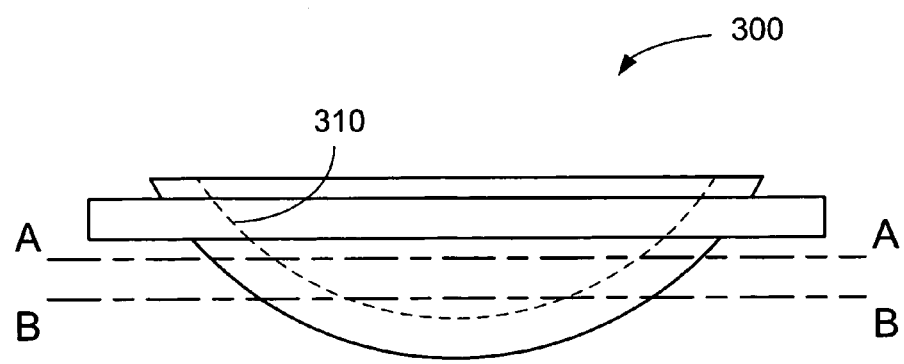
FIG. 3 depicts a side scanned image of a front curve mold.
Figure 4:
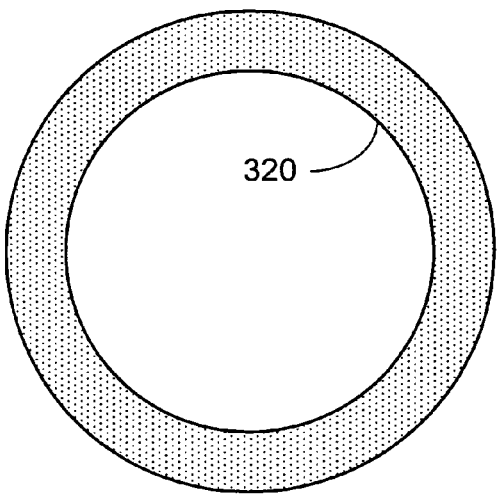
FIG. 4 depicts a slice plane image of the front curve mold of FIG. 3.
Figure 5:
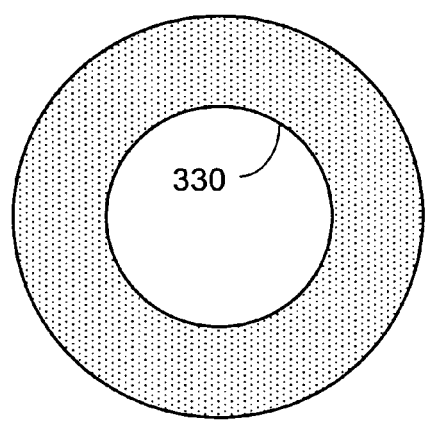
FIG. 5 depicts a second slice plane image of the front curve mold of FIG. 3.

As depicted in FIG. 3, a front curve mold 300 is scanned in multiple orientations and the data is processed. The data may be processed to compute the geometry of 2-dimensional slices through the object at sections A-A and B-B. The front curve optical surface 310 appears hidden in this view and is shown as a dashed line. The geometry of the 2-dimensional slice representations are shown in FIGS. 4 and 5. The inner edges 320, 330 of each slice represent the geometry of the front curve optical surface at each slice location. The optical surface 310 of the front curve mold is not visible when viewed from outside the mold along the sections A-A and B-B. The system and method is therefore capable of providing the geometry of surfaces which are obscured by other surfaces, or surfaces which are internal to the sample. Such measurement is very difficult with previous line of sight systems.

Figure 6:
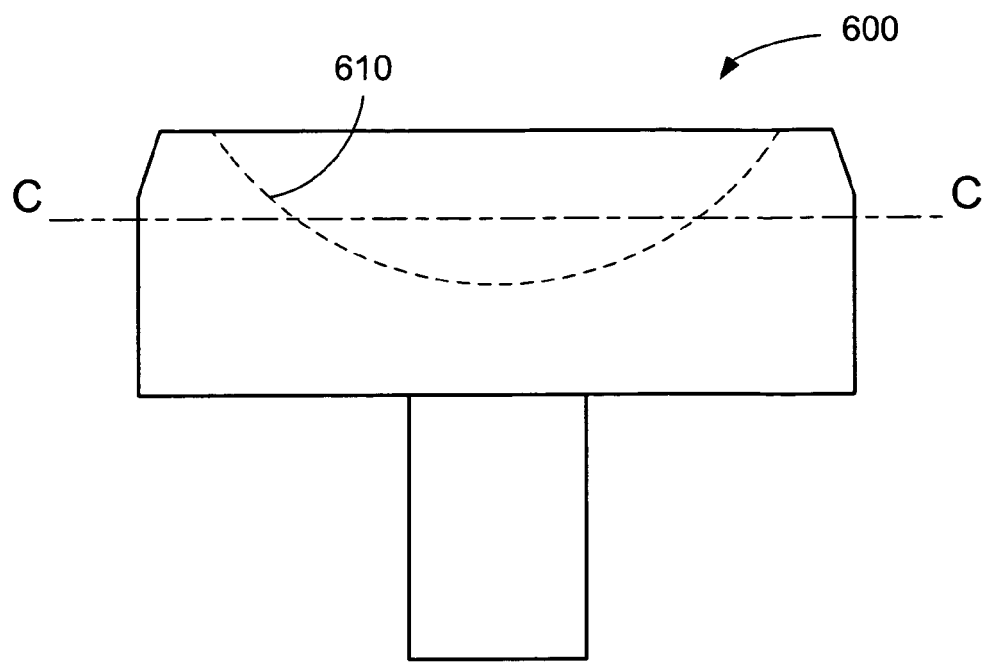
FIG. 6 depicts a side scanned image of a front curve optical tool.
Figure 7:
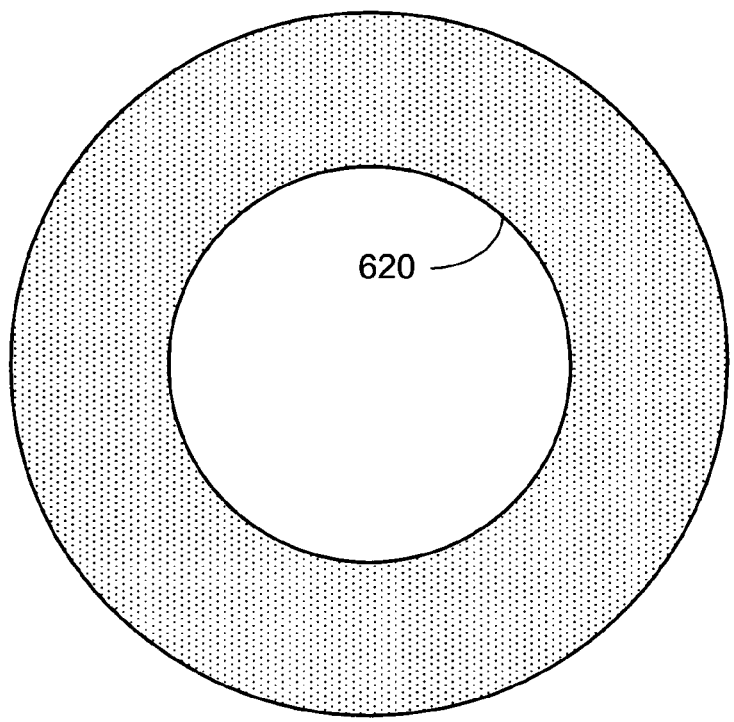
FIG. 7 depicts a slice plane image of the front curve optical tool of FIG. 6.

As depicted in FIG. 6, the present invention may also be used to scan an optical tool 600. The geometry of the inner optical surface 610 appears hidden in the view and is represented by a dashed line. FIG. 7 depicts a 2-dimensional slice through the optical tool 600 geometry computed along section C-C. The geometry of the inner optical surface 610 along the slice may then be reconstructed. The inner edge 620 represents the geometry of the inner optical surface at the slice location. All critical geometric dimensions of the optical tool 600 may be measured by reconstructing the necessary surfaces. For example, the alignment of a tool or the engraving marks may be measured. If the optical tool is scanned before molding, the tool surface may be compared to the resulting mold surface. This type of comparison may provide an accurate measurement of mold shrinkage. Non-axisymmetric shrinkage would not affect such analysis because the present invention allows the shrinkage to be calculated at multiple points over the entire surface. The present invention allows full measurement of the 3-dimensional shape, providing a deformation calculation across the optical surfaces at many different points.

In another embodiment of the present invention, the precise geometry of ophthalmic lenses may be obtained. The lenses may be scanned at any point in the manufacturing process. The uncured lens resin trapped between mating front curve and base curve mold halves may be scanned. The lens may be scanned a second time after the resin is cured. Finally, the completed lens may be scanned. During production, the lens may be inspected for defects such as trapped gas bubbles, inclusions in the lens material, or defects in the lens surface. The optical geometries of the completed lens may be compared against ideal dimensions and an optical quality value assigned to each lens. Mathematical algorithms may be written and executed on the PC to automatically detect defects, and flag any scanned lenses in which defects are found. As a final quality check, the completed lens may be scanned surrounded by a saline solution in the retail package prior to shipment.

In another embodiment of the present invention, the optical geometries of the completed lens obtained from the microCT process may be compared against ideal dimensions with optical quality values assigned to the key lens parameters. The optical quality values may then be used in a closed loop design system to iteratively modify the design geometry, the lens mold geometry, or the optical tool geometry. The resulting new lenses would then be scanned and the optical quality values evaluated. The process may then be automatically repeated until the completed lens geometry matches the desired lens geometry within a given quality tolerance.

In another embodiment of the present invention, the optical geometries of the completed lens obtained from the microCT process may be used to identify and quantify key non-geometric parameters in the manufacturing process. Illustrative examples of such non-geometric parameters are the quantity of liquid polymer placed in the mold, the duration and intensity of the lens curing process, and the material formulation of the lens polymers. The key parameters identified and quantified may then be used in a statistical process control methodology to yield a high precision manufacturing process which produces a high quality lens.

In another embodiment of the present invention, the wavelength of the electromagnetic radiation produced by the source may be optimized based upon the material of the sample being scanned. An aluminum optical tool may be scanned using a first radiation wavelength. A second wavelength may produce a more precise scan of a lens mold. Yet another wavelength may be employed in the scan of the cured or uncured lens polymer. Electromagnetic radiation in the range of wavelengths from about 1.0 micrometer to about 0.1 nanometer is useful in the present invention.

In another embodiment of the present invention, the material of the ophthalmic lens, the lens molds, or the optical tools may be changed or slightly altered in process to produce more accurate measurements by the scanning system. For example, a contrast agent, in the form of a filler material having a high electron density, may be added to the lens resin prior to molding to produce a lens with a high contrast during scanning. A similar filler material may be added to the material forming the lens mold. In another example, the lens may be soaked in a contrast agent such as an iodine solution after manufacture. Additionally, such changes may improve the signal to noise ratio in the collected data thus improving the geometric accuracy of the computed surfaces.

In another embodiment of the present invention, an ophthalmic lens may be placed on the human eye and scanned in vitro. The true optical geometry of the lens in use may then be readily quantified. The use of low radiation intensities and appropriate shielding will allow an acceptable level of exposure to the patient. A special lens may be prepared for the scan using a high contrast agent to allow for the accurate scanning of the lens optical surfaces while using the low radiation intensity. In alternative embodiments of the present inventions, the ophthalmic lens may be placed on the eye of a medical cadaver, or placed on a high fidelity model of the human eye and scanned.

The invention has been described in detail, with particular reference to certain preferred embodiments, in order to enable the reader to practice the invention without undue experimentation. A person having ordinary skill in the art will readily recognize that many of the previous components, compositions, and/or parameters may be varied or modified to a reasonable extent without departing from the scope and spirit of the invention. Furthermore, titles, headings, example materials or the like are provided to enhance the reader's comprehension of this document, and should not be read as limiting the scope of the present invention. Accordingly, the invention is defined by the following claims, and reasonable extensions and equivalents thereof.

What is claimed is:

1. A method for measuring the precise geometry of an ophthalmic sample comprising the steps of:

providing a source of electromagnetic radiation at an intensity, wherein said electromagnetic radiation is X-ray;

providing a detector to detect the electromagnetic radiation intensity;

positioning the sample such that the electromagnetic radiation generated by the source passes through the sample and to the detector, wherein the step of positioning the sample comprises positioning a contact lens on a human eye;

detecting the electromagnetic radiation intensity after passing through the sample; and processing the electromagnetic radiation intensity detected to obtain a 2-dimensional image of the sample, wherein said sample is a contact lens.

2. The method of claim 1, wherein:

the step of processing the electromagnetic radiation intensity further comprises processing the electromagnetic radiation intensity to obtain a 3-dimensional model of the sample surfaces, said model representing the precise 3-dimensional geometry of the sample surfaces.

3. The method of claim 2, wherein the step of processing the electromagnetic radiation intensity further comprises applying a sub-pixel edge detection algorithm to the electromagnetic radiation intensity.

4. The method of claim 1, wherein the step of positioning the sample occurs on a manufacturing line.

5. The method of claim 1, wherein the electromagnetic radiation is in the range of 1 micrometer to 0.1 nanometer.

6. The method of claim 2, further comprising archiving said precise geometry of the sample surfaces in a database application.

7. The method of claim 2, wherein the processed sample surface geometry is used in a feedback process to iteratively modify the geometry of a lens mold, or an optical tool.

8. The method of claim 2, wherein the processed sample surface geometry is used in a feedback process to iteratively modify a non-geometric parameter of the manufacturing process.

9. The method of claim 2, wherein the source of electromagnetic radiation is a micro-computed tomography scanner.

* * * * *